(12) United States Patent
Jovanov et al.

(10) Patent No.: US 7,928,835 B1
(45) Date of Patent: Apr. 19, 2011

(54) SYSTEMS AND METHODS FOR DRUG COMPLIANCE MONITORING

(75) Inventors: Emil Jovanov, Huntsville, AL (US); Robert Gold, Newburgh, IN (US)

(73) Assignee: The Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 575 days.

(21) Appl. No.: 11/958,345

(22) Filed: Dec. 17, 2007

Related U.S. Application Data

(60) Provisional application No. 60/870,282, filed on Dec. 15, 2006.

(51) Int. Cl.
*G08B 1/00* (2006.01)
*G08B 23/00* (2006.01)
*G04F 8/00* (2006.01)

(52) U.S. Cl. ............. 340/309.16; 340/309.7; 340/573.1; 705/2; 368/1; 368/10

(58) Field of Classification Search .............. 340/309.16
See application file for complete search history.

(56) References Cited

U.S. PATENT DOCUMENTS

| | | | |
|---|---|---|---|
| 4,223,801 A | 9/1980 | Carlson | |
| 4,616,316 A | 10/1986 | Hanpeter et al. | |
| 4,803,625 A | 2/1989 | Fu et al. | |
| 4,839,806 A | 6/1989 | Goldfischer et al. | |
| 4,899,839 A | 2/1990 | Dessertine et al. | |
| 4,933,873 A | 6/1990 | Kaufman et al. | |
| 4,942,544 A | 7/1990 | McIntosh et al. | |
| 5,016,172 A | 5/1991 | Dessertine | |
| 5,289,157 A | 2/1994 | Rudick et al. | |
| 5,646,912 A * | 7/1997 | Cousin ........................... 368/10 |
| 5,917,429 A | 6/1999 | Otis et al. | |
| 6,234,343 B1 * | 5/2001 | Papp ................................ 221/7 |
| 6,294,999 B1 * | 9/2001 | Yarin et al. ................. 340/573.1 |
| 6,985,869 B1 | 1/2006 | Stoll et al. | |
| 7,028,723 B1 | 4/2006 | Alouani et al. | |
| 7,158,011 B2 * | 1/2007 | Brue ........................ 340/309.16 |
| 2006/0041330 A1 | 2/2006 | Ansari et al. | |

OTHER PUBLICATIONS

Dr. Rahmat Shoureshi, "Smart Medication Dispenser-Aid for the Elderly," http://www.mines.edu/research/ott/pdfs/Smart%20Medication%2020Dispenser.pdf.

* cited by examiner

*Primary Examiner* — Donnie L Crosland
(74) *Attorney, Agent, or Firm* — Lanier Ford Shaver & Payne, P.C.; Jon E. Holland

(57) ABSTRACT

The present disclosure generally pertains to systems and methods for drug compliance monitoring. A drug compliance monitoring system in accordance with one exemplary embodiment of the present disclosure comprises a portable drug containment unit, which has a drug container, such as a pill bottle, for holding prescription or non-prescription drugs. The drug containment unit also comprises at least one sensor and control logic. The sensor is configured to automatically sense a parameter indicating when a drug, such as one or more pills or an amount of liquid, has been or is about to be removed from the drug container. The system, based on the sensor, automatically estimates and tracks drug consumption and provides a patient with reminders when a dosage is currently due. If the patient deviates from an expected drug regime, the system automatically senses this event and provides a notification to the patient or caregiver. In addition, the system stores a usage history indicating the approximate time and amount of each sensed dosage.

31 Claims, 7 Drawing Sheets

(Side View)

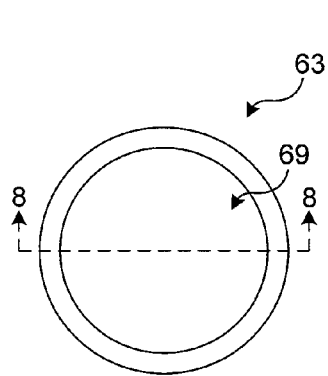
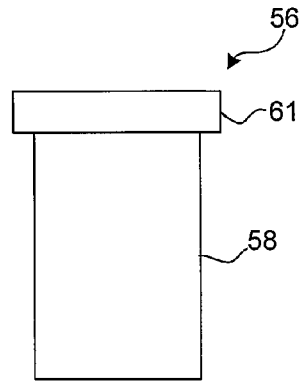
FIG. 3 (Top View)
FIG. 4 (Side View)
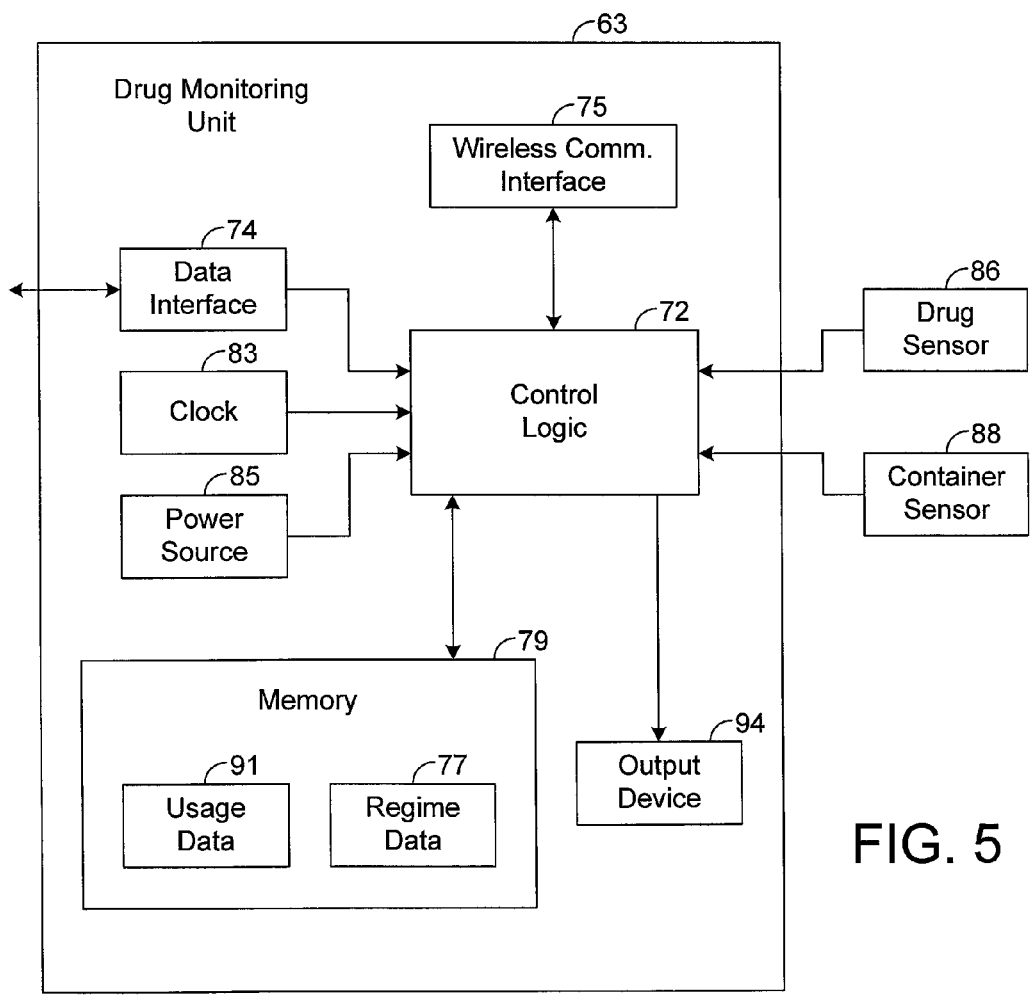
FIG. 5

(Top View)

SYSTEMS AND METHODS FOR DRUG COMPLIANCE MONITORING

CROSS REFERENCE TO RELATED APPLICATION

This application claims priority to U.S. Provisional Application No. 60/870,282, entitled "Systems and Methods for Drug Compliance Monitoring," and filed on Dec. 15, 2006, which is incorporated herein by reference.

RELATED ART

Drug compliance is a critical element to various medical treatments and research. Indeed, certain drugs lose their effectiveness or can have relatively severe side-effects if they are not administered according to a drug regime prescribed by a physician or pharmacist. In addition, the results of a medical research study can be skewed if the participants do not consume the medication being researched as prescribed.

There are various reasons why a patient may deviate from a prescribed drug regime. For example, a patient may simply forget to take one or more dosages, or a patient may misread or misunderstand the instructions prescribed by a physician or pharmacist. The risk of deviating from a prescribed treatment plan generally increases as the number of drugs involved in the treatment plan increases, which is typical for chronic diseases. In this regard, a patient may be expected to take dosages of different amounts and different times of the day for different drugs. Remembering which drugs have been taken and the correct dosage amounts and times for the different drugs can be problematic and confusing. In addition, a patient may be suffering from an illness or a condition that affects his or her memory or cognitive abilities. Ensuring that such a patient adheres to a prescribed treatment plan can be particularly problematic.

Various attempts have been made to address some of the problems associated with drug compliance. For example, some proposed systems attempt to track the dosages taken by a patient so that a determination can be made as to whether the patient is complying with a particular drug regime. However, such systems can be relatively expensive, complex to operate or set-up, and/or rely too heavily on patient compliance and/or manual or semi-automatic data entry. For example, U.S. Pat. No. 4,899,839 describes an embodiment of a drug compliance monitoring system that tracks the weight of a medicine bottle to compliance with a medicine regime. In such an embodiment, the patient or caregiver places the medicine bottle on a scale from time-to-time so that the weight of the bottle can be ascertained. Thus, the system appears to rely on the patient or caregiver's memory and/or willingness to cooperate in the monitoring process.

Better and more automated systems and methods for monitoring drug compliance are generally desired.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 3 is a top view illustrating an exemplary drug monitoring unit, such as is depicted by FIG. 2.

FIG. 4 is a side view illustrating an exemplary drug container, such as is depicted by FIG. 2.

FIG. 5 is a block diagram illustrating an exemplary drug monitoring unit, such as is depicted by FIG. 3.

DETAILED DESCRIPTION

The present disclosure generally pertains to systems and methods for drug compliance monitoring. A drug compliance monitoring system in accordance with one exemplary embodiment of the present disclosure comprises a portable drug containment unit, which has a drug container, such as a pill bottle, for holding prescription or non-prescription drugs. The drug containment unit also comprises at least one sensor and control logic. The sensor is configured to automatically sense a parameter indicating when a drug, such as one or more pills or an amount of liquid, has been or is about to be removed from the drug container. The system, based on the sensor, automatically estimates and tracks drug consumption and provides a patient with reminders when a dosage is currently due. If the patient deviates from a prescribed drug regime, the system automatically senses this event and provides a notification to the patient or caregiver, such as a relative, friend, nurse, pharmacist or physician, for example. In addition, the system stores a usage history indicating the time and approximate amount of each sensed dosage.

Figure 1:
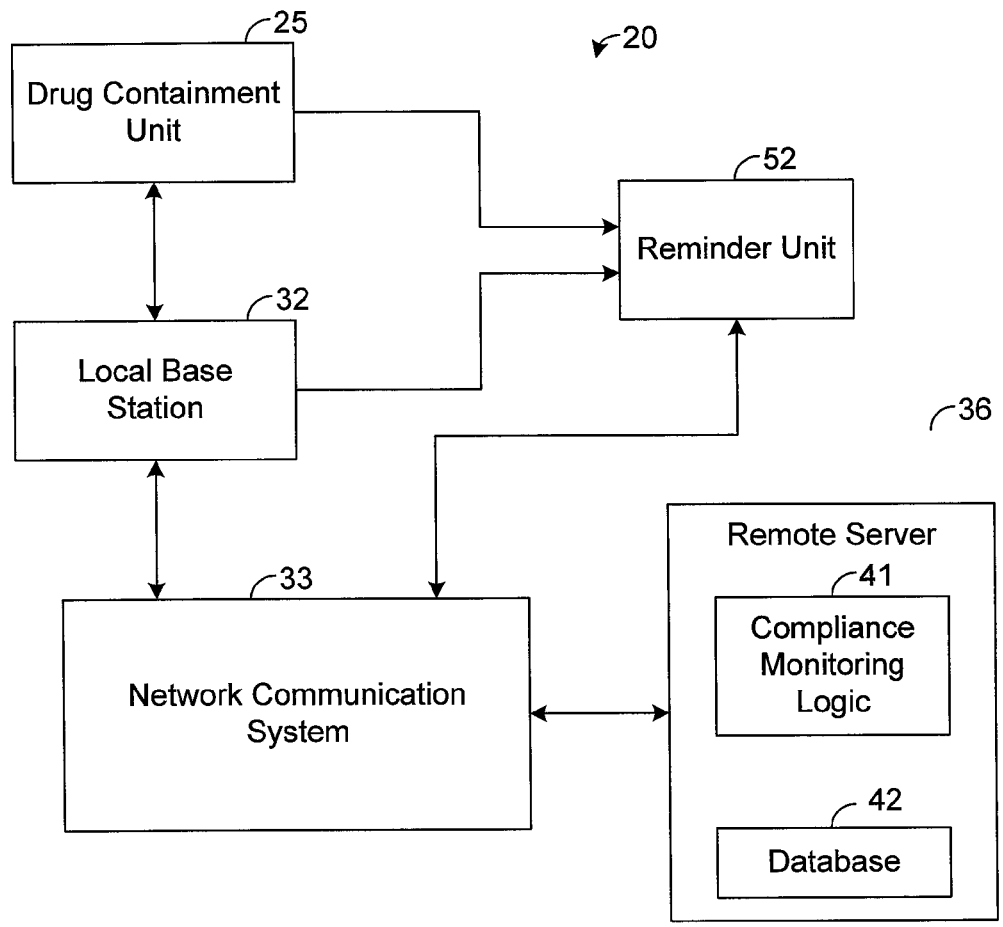
FIG. 1 is a block diagram illustrating an exemplary drug compliance monitoring system.

FIG. 1 depicts an exemplary embodiment of a drug compliance monitoring system 20. As shown by FIG. 1, the system 20 comprises a drug containment unit 25 for holding a drug in either a solid (e.g., pills or powder), gas, or liquid form. As will be described in more detail hereafter, the unit 25 is embedded with intelligence that automatically monitors one or more conditions indicative of when a patient is likely consuming the drug held by the unit 25.

The drug containment unit 25 is communicatively coupled to a local base station 32. In one exemplary embodiment, a wireless radio frequency (RF) link is used to communicate between the drug containment unit 25 and the local base station 32. However, other types of wireless and/or non-wireless links may be used in other embodiments.

In one exemplary embodiment, the local base station 32 resides at the home of the patient who is taking the drug held by the unit 25, but other locations of the local base station 32 are possible in other embodiments. For example, the local base station 32 may be implemented via a desk-top, lap-top computer, personal digital assistant (PDA), or cell phone that is within the transmission range of the drug containment unit 25. In another example, the local base station 32 is implemented via a router that routes messages to and from the drug containment unit 25.

As shown by FIG. 1, the local base station 32 is communicatively coupled to a network communication system 33, which comprises at least one wide area network (WAN) communication system, such as the Internet. However, the network communication system 33 may comprise other types of networks in addition to or in lieu of the Internet. For example, the system 33 may comprise the public switched telephone network (PSTN) and/or a cellular telephone network.

Located remotely from the local base station 32 and communicatively coupled to the network communication system 33 is a remote server 36, which has compliance monitoring logic 41 and a database 42. Notifications indicative of the dosages taken by the patient are transmitted to the remote server 36 via the local base station 32 and the network communication system 33. The compliance monitoring logic 41 compares such information to data indicative of an expected drug regime associated with the drug in the containment unit 25. Based on such comparisons, the compliance monitoring logic 41 provides reminders about when a dosage is to be taken and/or notifications about deviations from the expected drug regime in an effort to ensure compliance to such regime. For example, if the compliance monitoring logic 41 determines that a dosage is due, the logic 41 transmits a notification (referred to herein as a "reminder notification") to a mobile reminder unit 52, which is carried by the patient. The reminder notification can be sent directly from the server 36 or through local base station 32. In another example, control logic 72 of the drug monitoring unit 63 determines when a dosage is due and transmits a reminder notification to the reminder unit 52. Such reminder notification can be transmitted directly to the reminder unit 52 or through the local base station 32 and/or network communication system 33.

In response to the reminder notification, the reminder unit 52 displays a message or other type of indication to remind the patient to take a dosage of the drug in the unit 25. Such a message may identify the dosage time, dosage amount, suggested use (e.g., before or after a meal), and drug type (e.g., the name of the drug, shape and color of the drug, location of the drug bottle defined by user or caregiver, etc.). If desired, the reminders and other notifications may be transmitted by the drug containment unit 25 rather than a compliance monitoring logic that is external to the unit 25.

In one exemplary embodiment, the reminder unit 52 is implemented via a cellular telephone, pager, or electronic mail device, and the remote server 36 or drug containment unit 25 provides a dosage reminder by transmitting a message directly or through the network communication system 33 to the reminder unit 52, which then displays the text message. In other embodiments, other types of messages or indications may be provided by the system 20.

Figure 2:
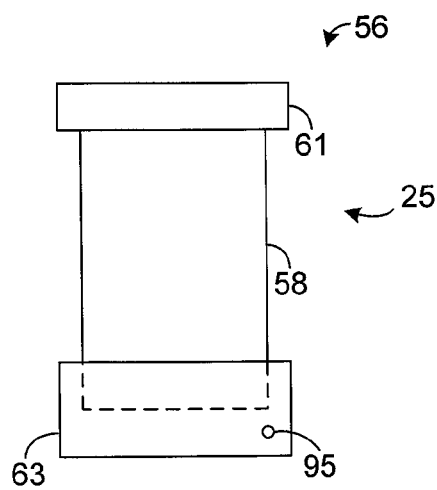
FIG. 2 is a side view illustrating an exemplary drug containment unit, such as is depicted by FIG. 1.

FIG. 2 depicts an exemplary embodiment of a drug containment unit 25. The unit 25 comprises a drug container 56 (e.g., a pill bottle) comprising a container body 58 and a cap 61, which is screwed or otherwise attached to the container body 58. The container body 58 is integrated with or detachably coupled to a drug monitoring unit 63. In one exemplary embodiment, as shown by FIG. 3, the drug monitoring unit 63 has a frame 66 that is composed of plastic or some other material. The frame 66 has a cavity 69 into which a bottom of the container body 58 fits. Note that FIG. 3 shows a top view of the frame 66 when the container 56 has been removed from the drug monitoring unit 63, and FIG. 4 shows the container 56 after it has been removed from the drug monitoring unit 63.

In one exemplary embodiment, the circumference of the cavity 69 is just larger than that of the bottom of the container body 58 such that the body 58 snugly fits in the frame 66 and is held in place by frictional forces between the frame 66 and body 58. The frictional forces are sufficient to keep the frame 66 attached to the body 58 if the drug container 56 is picked up by a user, such as when a user picks up the container 56 in order to extract a drug dosage. However, a user may separate the body 58 from the frame 66 and, therefore, the drug monitoring unit 63 by pulling apart the frame 66 and the body 58 by hand. In other embodiments, other techniques for detachably coupling the frame 66 to the body 58 are possible. For example, the interior cavity walls of the frame 66 and the exterior of the container bottom may be threaded such that the body 58 is screwed into the frame 66. In such an embodiment, the frame 66 can be separated from the body 58 by unscrewing the frame 66.

As shown by FIG. 5, the drug monitoring unit 63 comprises control logic 72, which generally controls the operation of the unit 63. The control logic 72 is configured to communicate with a data interface 74 and a wireless communication interface 75. The control logic 72 receives regime data 77 from the data interface 74 and stores the regime data 77 in memory 79. Various types of interface devices, such as a universal serial bus (USB) port, may be used to implement the data interface 74. The regime data 77 is indicative of a desired drug regime for the drug held by the container 56. For example, the regime data 77 may indicate the time and drug amount of each desired dosage of the drug regime. Thus, the data 77 can be analyzed to determine when and how much of a drug held by the container 56 is to be taken in order to comply with the desired drug regime.

The wireless communication interface 75 is configured to communicate wireless signals. In one exemplary embodiment, the interface 75 is configured to communicate RF signals, but other types of signals may be communicated by the interface 75 in other embodiments.

As shown by FIG. 5, the drug monitoring unit 63 comprises a clock 83 that provides the control logic 72 with timing information, such as the current time of day. The unit 63 also comprises a power source 85, such as a battery, that provides electrical power to the other electrical components of the unit 63 and/or the container 56. In addition, the control logic 72 is configured to receive information from a drug sensor 86 and a container sensor 88. The container sensor 88 is configured to detect a parameter indicative of when a user is likely extracting a drug dosage from the container 56. For example, in one embodiment, the sensor 88 comprises a mechanical switch (not shown in FIG. 5) that senses when the cap 61 (FIG. 4) has been removed from the container body 58. Such an event indicates that the user is likely removing a dosage of the drug held by the container 56. In another embodiment, the sensor 88 is capacitive and is able to sense when a user has grasped the container body 58 or the cap 61. In another embodiment, the sensor 88 comprises an accelerometer, which senses when the container 56 is being moved, such as when a user has picked up the container 56 in order to remove a dosage from the container 56.

The drug sensor 86 is configured to sense a parameter indicative of an amount of a drug held by the container 56. For example, in one embodiment, the sensor 86 comprises a weight scale, which senses a weight of the container 56, including the drug held by the container 56. Moreover, changes in the sensed weight indicate when and how much of a drug is removed by a user.

Figure 6:
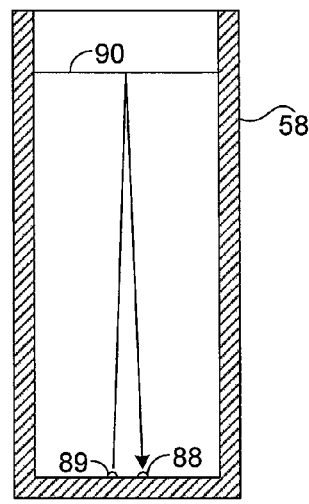
FIG. 6 is a cross-sectional view of a drug container, such as is depicted by FIG. 2.

In another embodiment, the sensor 88 comprises an ultrasonic receiver. For example, FIG. 6 shows a cross-sectional view of an exemplary embodiment of the container body 58. An ultrasonic emitter 89 at the bottom of the container 56 emits an acoustic signal through the drug. The signal reflects at the surface 90 of the drug, and the sensor 88, which is located at the bottom of the container 56, receives the reflected signal. Further, the control logic 72 measures the time from transmission to reception. The greater the time, the more drug is within the container 56. Thus, the control logic 72 estimates the volume of the drug within the container 56 based on the sensed time period.

In another embodiment, the sensor 86 is capacitive. In this regard, the sensor 86 comprises a plurality of electrodes, and the sensor 86 is configured to measure changes in capacitance between electrodes. Changes in the amount of the drug within the container 56 affect the sensed capacitance so that the volume of the drug can be estimated by the control logic 72 based on the sensed capacitance.

In yet another embodiment, a transmitter may emit an acoustic signal that causes vibrations in the container 56, and the sensor 86 comprises an accelerometer, piezoelectric sensor, or some other device for measuring the vibration. The resonant frequency of such vibrations depends on the volume of the drug within the container 56 so that the resonant frequency is an indicator of the amount of the drug within the container 56. Moreover, the transmitter sweeps through a range of frequencies until the resonant frequency is detected by the sensor 86. The control logic 72 is configured to determine that the transmission frequency resulting in the greatest amount of sensed vibration is the container's current resonant frequency, and changes in the resonant frequency indicate changes in the amount of drug within the container 56. Thus, based on the sensed vibrations, the control logic 72 estimates the amount of drug in the container 56.

Moreover, based on the sensors 86, 88, the control logic 72 determines when a user is taking a dosage of the drug held by the container 56 and estimates the amount of drug taken for each dosage. The control logic 72 is configured to maintain a history of the dosages taken by the user. In this regard, the control logic 72 stores usage data 91 in memory 79, and the control logic 72 is configured to update the usage data 91 for each dosage sensed by the monitoring unit 63. In particular, for each sensed dosage, the control logic 72 determines the time of the dosage, based on the clock 83, and determines the amount of the drug taken based on the drug sensor 86. The control logic 72 then updates the data 91 with such information.

In some cases, depending on the type of drug in the container 56, the expected dosage amounts, and the techniques used to sense the drug amount held by the container 56, the control logic 72 is able to detect changes in the drug amount for each dosage. However, in other cases, resolution of the drug sensor 86 may be insufficient to enable the logic 72 to sense a change in the amount of drug in the container 56 for each dosage. In such a case, the control logic 72 may be configured to sense a change in the drug amount over several dosages and average the change in order to determine a per dosage drug change. For example, if the control logic 72 determines that the drug weight changes by 5 milligrams over 5 dosages, the control logic 72 may determine that the user took 1 milligram per dosage.

By comparing the regime data 77 to the usage data 91, the control logic 72 determines whether the user is deviating from the desired drug regime indicated by the data 77. The control logic 72 also determines when it is time for the user is to take a dosage in order to comply with the desired drug regime.

It should be noted that the database 42 can be used to store various types of information, such as information indicative of the expected drug regime or drug usage, as determined based on information from the drug monitoring unit 63. In one exemplary embodiment, the database 42 stores various rules about drug consumption for many different drug types, and such rules are used to establish the desired drug regime for a particular patient. For example, for a particular drug, the database 42 may store data indicating different dosage amounts per dosage and/or different dosage frequencies for patients depending on various patient characteristics, such as the patient's age, gender, and/or weight. In one exemplary embodiment, such patient characteristics, as well as the drug type of the drug held by the container 56, are downloaded into the drug monitoring unit 63, and the control logic 72 is configured to access the rules correlated with the downloaded patient characteristics and drug type in order to define the regime data 77 (e.g., the expected dosage amounts and dosage times). In other embodiments, the patient characteristics are input to the system 20 elsewhere. For example, a physician or other user at the remote server 36 may input the patient characteristics and define the appropriate regime data 77 for the drug monitoring unit 63 based on the rules stored in the database 42. The regime data 77 may then be downloaded from the server 36 to the unit 63 through the network communication system 33 and local base station 32 or otherwise.

Although the regime data 77 may be automatically defined based on the drug consumption rules at the remote server 36, the system 20 allows the drug consumption rules to be manually overridden. For example, a physician at the remote server 36 may decide that a particular patient should have a drug regime different than that indicated by the drug consumption rules stored at the remote server 36. In such an embodiment, the physician may define a set of rules specifically for such patient such that when the patient's monitoring unit 63 accesses the drug consumption rules, the regime data 77 is defined by the rules specifically tailored for the patient. In such an example, a patient identifier may be stored in the database 42 and used by the patient's monitoring unit 63 when accessing the drug consumption rules.

In another example, a physician or other user at the remote server 36 provides an input for modifying the drug regime data 77 already stored in the drug monitoring unit 63. Information indicative of the input is communicated to the monitoring unit 63, and the control logic 72 updates the regime data 77 based on such information. Note that the regime data 152 at the remote server 36 may be similarly defined and/or updated as described above for the regime data 77 stored in the drug monitoring unit 63.

When the control logic 72 determines that it is time for a dosage, based on the regime data 77 or otherwise, the control logic 72 provides an indication via an output interface 94 (FIG. 5). In one exemplary embodiment, the output interface 94 comprises at least one light source, such as a light emitting diode (LED). Indeed, FIG. 2 depicts or exemplary embodiment in which an LED 95 is used to implement at least a portion of the output interface 94. In order to indicate that it is time for a dosage, the control logic 72 activates the light source 95 such that it emits light. Accordingly, if the drug containment unit 25 is kept next to other similar units 25, a user can easily discern, based on the state of the output interface 94 for each unit 25, which units 25 have drugs that are to be taken immediately. In other embodiments, the output interface 94 can comprise other types of devices. For example, the output interface 94 may comprise a liquid crystal display (LCD) or other type of device that allows the display of textual messages. In such an embodiment, the output interface 94 may indicate not only that it is time for a dosage of the drug held by the container body 58, but the output interface 94 may also indicate the desired amount of the dosage or prescribed use. For example, the output interface 94 may indicate that the user is to take a certain number of pills or a certain volume of the drug for the current dosage thereby helping the user to comply with the desired drug regime. In other embodiments, the output interface 94 comprises a speaker, which provides audio output, such as a buzzer or pre-recorded message, for example.

Figure 7:
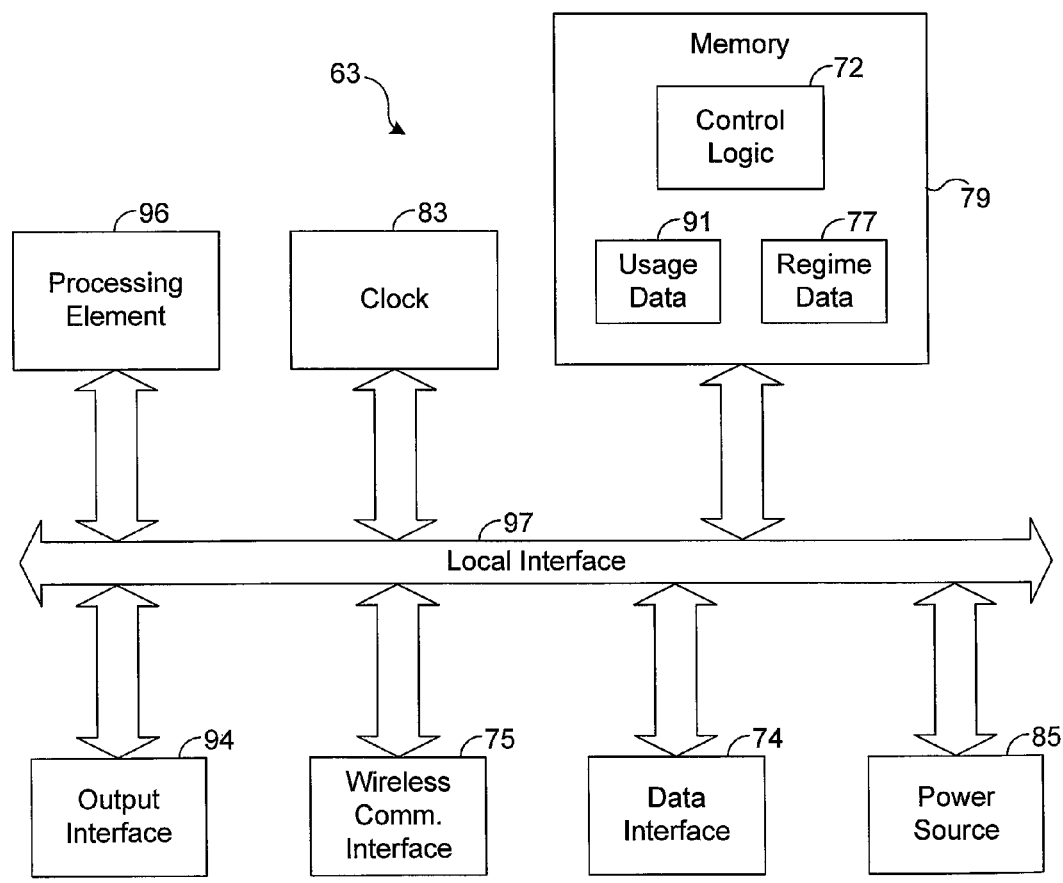
FIG. 7 is a block diagram illustrating an exemplary drug monitoring unit, such as is depicted by FIG. 5.

It should be noted that the control logic 72 can be implemented in software, hardware, or a combination thereof. In an exemplary embodiment illustrated in FIG. 7, the control logic 72 is implemented in software and stored in memory 79. The control logic 79, when implemented in software, can be stored and transported on any computer-readable medium.

The exemplary embodiment of the drug monitoring unit 63 depicted by FIG. 6 comprises at least one conventional processing element 96, such as a central processing unit (CPU), that communicates to and drives the other elements within the apparatus 95 via a local interface 97, which can include at least one bus. The processing element 96 is configured to execute instructions of the control logic 72, when such logic 72 is implemented in software.

Figure 8:
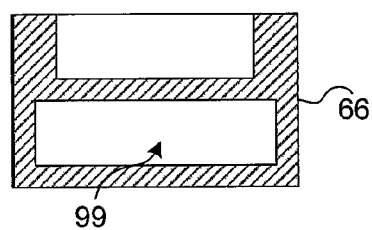
FIG. 8 is a cross-sectional view of the drug monitoring unit depicted by FIG. 3.

Note that the various components of the drug monitoring unit 63 can be housed by the frame 66 (FIG. 3). For example, in one embodiment, as shown by FIG. 8, the frame 66 has a cavity 99, which is completely enclosed by the frame 66, although it is unnecessary for the cavity 99 to be completely enclosed by the frame 66 in other embodiments. The control logic 72, memory 79, wireless communication interface 75, clock 83, and power source 85 reside in the cavity 99, although it is possible for any of the foregoing components to be positioned at other locations in other embodiments.

Figure 9:
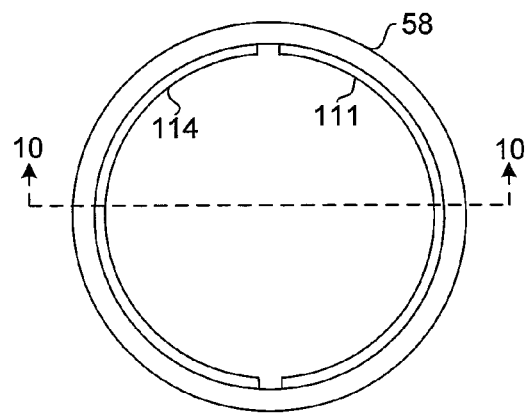
FIG. 9 is a top view of the drug container depicted by FIG. 4 with a cap of the drug container removed.
Figure 10:
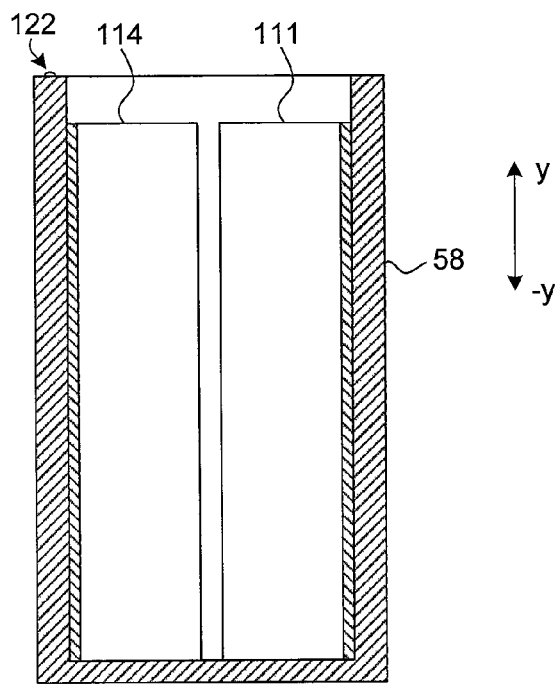
FIG. 10 is a cross-sectional view of the drug container depicted by FIG. 9.
Figure 11:
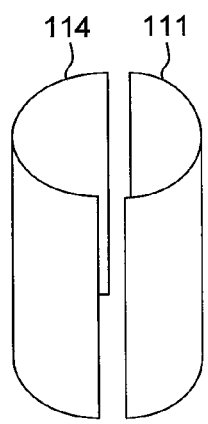
FIG. 11 depicts a plurality of electrodes depicted in FIG. 10 with the drug container removed for illustrative purposes.

As described above, various types of techniques may be employed to estimate an amount of the drug held by the container 56. In one exemplary embodiment, which will be described in more detail below, capacitive sensing is used to sense the amount of the drug held by the container 56. In this regard, as shown by FIGS. 9 and 10, the drug sensor 86 comprises a pair of electrodes 111, 114 positioned on opposite sides of the interior wall of the container body 58. FIG. 11 shows the electrodes 111, 114 with the body 58 removed for illustrative purposes. Each electrode 111, 114 is implemented as a curved conductive plate in the embodiment shown by FIGS. 9-11, but other types of electrodes (e.g., other conductive patterns) are possible in other embodiments.

It should be noted that the sensor 86 may comprise other numbers of electrodes and other positions of the electrodes are possible in other embodiments. For example, it is possible for the electrodes 111, 114 to be embedded in the wall of the container body 58. Further, the container body 58 is preferably manufactured with conductive traces that run from the electrodes 111, 114 through the wall of the body 58 and are exposed at the bottom of the container body 58 where the body joins the drug monitoring unit 63. In addition, the drug monitoring unit 63 has exposed conductive traces that run to the control logic 72.

Moreover, during a measurement cycle, the control logic 72 is configured to provide a constant current that flows through the electrodes 111, 114, and the control logic 72 measures the voltage difference between the two electrodes 111, 114. The measured voltage in time varies with changes in capacitance, and capacitance varies depending on the amount of drug, whether in solid or liquid form, in the container 56. Accordingly, the measured voltage is indicative of the capacitance of the electrodes 111, 114 and, therefore, of the amount of drug that is between the electrodes 111, 114. In another implementation, the logic 72 is configured to measure the time to achieve a certain voltage as defined as a measurement threshold, which is essentially equivalent to the previously described voltage measurement.

Note that it is likely that the electrodes 111, 114, as well as the entire drug container 56, are relatively inexpensive compared to the components of the drug monitoring unit 63. Moreover, it is possible for the drug container 56 to be disposable, and for the drug monitoring unit 63 to be re-used for different containers 56. For example, in filling a prescription, a pharmacist may provide the drug containment unit 25 shown by FIG. 2 to a user, referred to hereafter as the "patient," with the appropriate amount of drug in the container 58 for the prescription. The pharmacist may also download the regime data 77 to the drug monitoring unit 63 via the data interface 74. Such data 77 indicates the times and amounts of dosages that are expected for the prescription being filled.

Thereafter, the user may utilize the drug containment unit 25 to comply with the expected drug regime indicated by the prescription, as described herein. Once the regime has ended or the container 56 is emptied, the user may then detach the container 56 from the drug monitoring unit 63 and dispose of the container 56. Later, the user may take the drug monitoring unit 63 back to the pharmacist when another prescription is to be filled, and the pharmacist may attach, to the unit 63, a new container 56 holding a new drug for the new prescription. Since the drug container 56 and the electrodes 111, 114 are relatively inexpensive, disposing of the first container 56 and using a new container 56 for the new prescription is not very costly. However, using a new container 56 for the new drug helps to ensure that remnants of the old drug are not mixed with the new drug, as could be the case if the same container 56 was used for both drugs.

As described above, the determination that the patient has taken a dosage of the drug held in the container 56 may be based on the drug sensor 86 and/or the container sensor 88. FIG. 10 depicts an exemplary embodiment in which the container sensor 88 is implemented via a spring-loaded switch 122. In this regard, when the cap 61 is placed on the container body 58, the cap 61 moves the switch 122 in the negative (−) y-direction. When the cap 61 is removed from the body 58, a spring (not specifically shown in FIG. 10) moves the switch 122 in the y-direction. Thus, the state of the switch 122 indicates whether the cap 61 is on or off of the body 58. Various known or future-developed switches may be used to sense when the cap 61 is removed from the body 58. In one exemplary embodiment, the control logic 72 determines that a dosage has been taken when it determines that, based on switch 122, the cap 61 is off of the body 58 and that the capacitance of the electrodes 111, 114 has changed in a manner that indicates the amount of drug in the body 58 has reduced while the cap 61 is off of the body 58.

Figure 12:
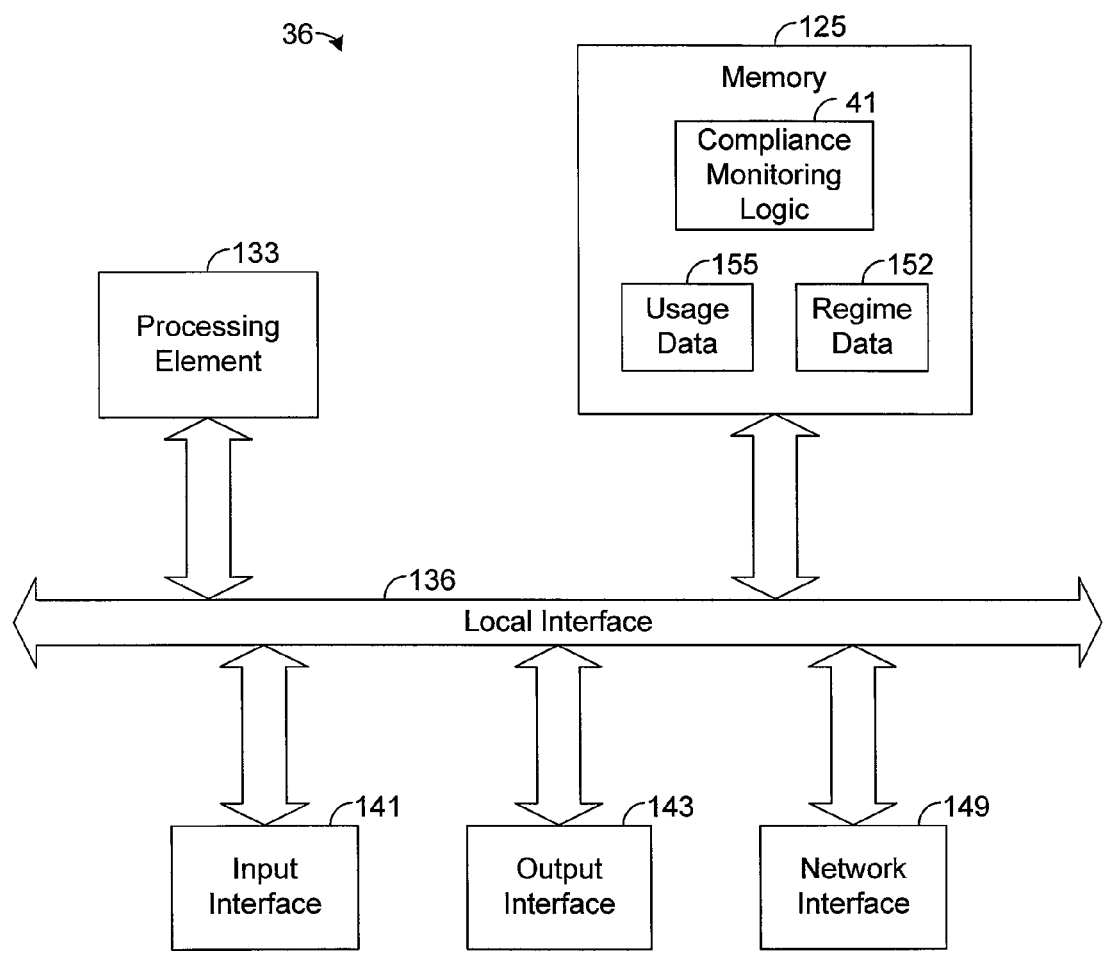
FIG. 12 is a block diagram illustrating an exemplary remote server, such as is depicted by FIG. 1.

FIG. 12 depicts an exemplary embodiment of the remote server 36. The compliance monitoring logic 41 can be implemented in software, hardware, or a combination thereof. In the exemplary embodiment depicted by FIG. 12, the compliance monitoring logic 41 is implemented in software and stored in memory 125. The compliance monitoring logic 41, when implemented in software, can be stored and transported on any computer-readable medium.

The exemplary embodiment of the remote server 36 depicted by FIG. 12 comprises at least one conventional processing element 133, such as a central processing unit (CPU), that communicates to and drives the other elements within the server 36 via a local interface 136, which can include at least one bus. The processing element 133 is configured to execute instructions of the compliance monitoring logic 41, when such logic 41 is implemented in software. Furthermore, an input interface 141, for example, a keyboard, a mouse, or a keypad, can be used to input data from a user of the server 36, and an output interface 143, for example, a printer, a speaker, or a display device, such as liquid crystal display (LCD), can be used to output data to the user. The server 36 also comprises a network interface 149 that allows the server 36 to exchange information with the network communication system 33 (FIG. 1).

As shown by FIG. 12, regime data 152 is stored in the memory 125. The regime data 152, like the regime data 77 (FIG. 5) stored in the drug monitoring unit 63, indicates the desired drug regime to be followed by the patient. For example, the regime data 152 may indicate the time, drug amount, and use for each expected dosage. As described in more detail hereinbelow, the drug monitoring unit 63 is configured to send, to the remote server 36, updates indicating when the patient has taken dosages and how much of the drug in the container 56 is removed for each dosage. The compliance monitoring logic 41 stores, in memory 125 as usage data 155, the information received from the drug monitoring unit 63. Thus, by comparing the usage data 155 to the regime data 152, the logic 41 can determine whether the patient is complying with a desired drug regime, when the patient should take a new dosage, and when the patient misses a dosage. Note that the usage data 155 and/or the regime data 152 may be stored in a database 42, such as is depicted by FIG. 1, or in other types of memory. As described above, the memory 125 may also contain rules and dosages for many different drugs and drug regimes.

The compliance monitoring logic 41 is configured to take various actions depending on the manner in which the patient takes the drug in the container 56. For example, the logic 41 may send or display notifications indicative whether and to what extent the patient is complying with the drug regime indicated by the data 152. Any such notification may include the history (e.g., times and amounts) of dosages detected by the drug monitoring unit 63. In another example, a notification simply indicates whether or not the patient is complying with the drug regime without providing a history of the dosages. If the logic 41 determines that the patient has missed a dosage, the logic 41 may transmit or display a notification of such event.

Various types of people may receive the notifications transmitted or displayed by the compliance monitoring logic 41. For example, the notifications may be sent or displayed to the patient, the patient's doctor, nurse, pharmacist or other caregiver, and/or to a friend or relative of the patient. Any notification may be displayed locally at the server 36 or transmitted remotely via the network communication system 33. In addition, it is unnecessary for the same network to be used to receive updates from the drug monitoring unit 63 and to transmit the notifications from the compliance monitoring logic 41. For example, an update may be received via the Internet and a notification may be transmitted via the Internet, a cellular telephone call, or otherwise.

In one exemplary embodiment, the compliance monitoring logic 41 or the drug monitoring unit 63 transmits a notification, to the reminder unit 52, when it is time or about time for the patient to take a dosage or when it is determined that the patient has missed a dosage. Such notification may indicate the time period in which the dosage is scheduled to be taken. The notification may be an email, text message, or some other type of message, such a recorded audio message transmitted via a cellular telephone network or other type of telephone network.

Figure 13:
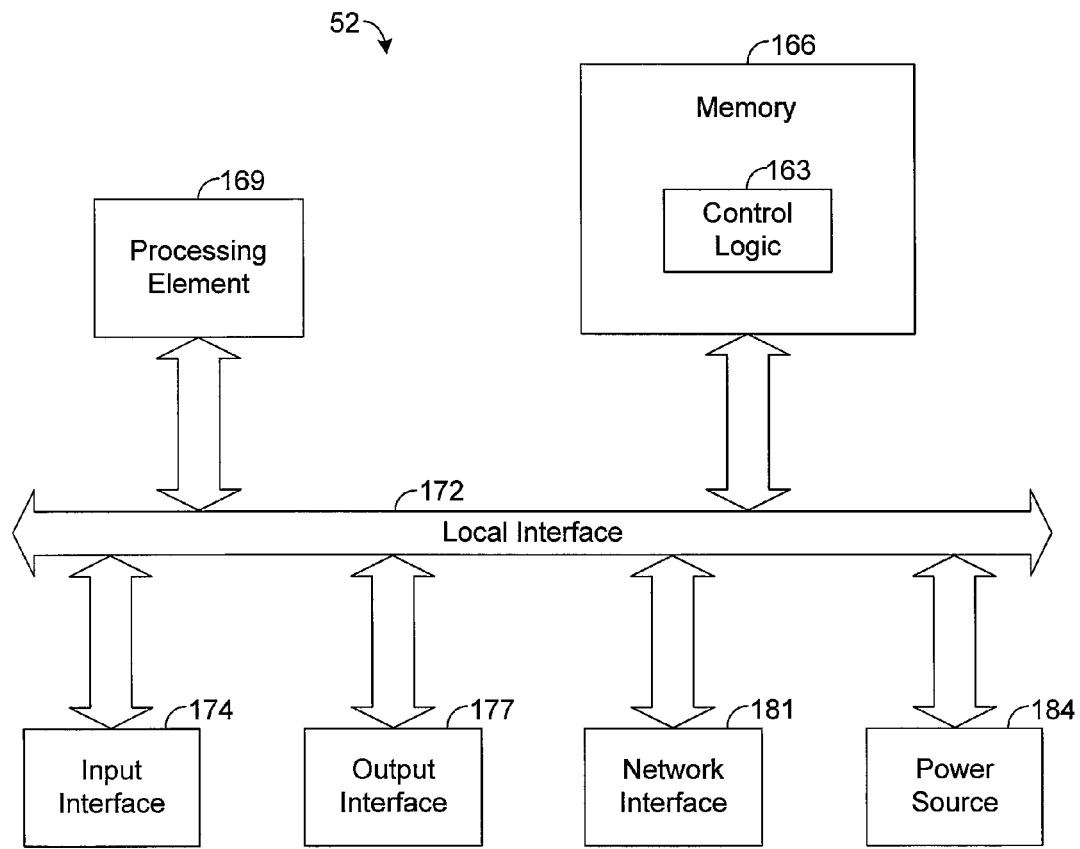
FIG. 13 is a block diagram illustrating an exemplary reminder unit, such as is depicted by FIG. 1.

FIG. 13 depicts an exemplary embodiment of the reminder unit 52. The reminder unit 52 is preferably implemented as a cellular telephone, a pager, a lap-top computer, a personal digital assistant (PDA), or some other portable device, although it is possible for the reminder unit 52 to be implemented as a stationary device, such as a desk-top computer.

As shown by FIG. 13, the reminder unit 52 comprises control logic 163 that is configured to generally control the operation of the unit 52. The control logic 163 can be implemented in hardware, software, or a combination thereof. In the exemplary embodiment depicted by FIG. 13, the control logic 163 is implemented in software and stored in memory 166. The control logic 163, when implemented in software, can be stored and transported on any computer-readable medium.

The exemplary embodiment of the reminder unit 52 depicted by FIG. 13 comprises at least one conventional processing element 169, such as a central processing unit (CPU), that communicates to and drives the other elements within the unit 52 via a local interface 172, which can include at least one bus. The processing element 169 is configured to execute instructions of the control logic 163, when such logic 163 is implemented in software. Furthermore, an input interface 174, for example, a keyboard, a mouse, or a keypad, can be used to input data from a user (e.g., the patient) of the unit 52, and an output interface 177, for example, a printer, a speaker, or a display device, such as liquid crystal display (LCD), can be used to output data to the user. The unit 52 also comprises a network interface 181 that allows the unit 52 to exchange information with the network communication system 33. In addition, the unit 52 comprises a power source 184, such as a battery, that provides electrical power to the other components of the unit 52.

Upon receiving a notification from the compliance monitoring logic 41 or the drug monitoring unit 63, the control logic 163 of the reminder unit 52 is configured to interface the notification with the patient. For example, the control logic 163 may display the notification via the output interface 177. In some cases, the notification may include an audio message that is played via a speaker of the output interface 177, such as when the notification is communicated via cellular signals.

Note that the compliance monitoring logic 41 may reside at locations other than the remote server 36. For example, the compliance monitoring logic 41 may reside at the local base station 32 or the reminder unit 52. In such an example, the notification may be transmitted to the reminder unit 52 via wireless signals, such as RF signals, or non-wireless signals without being communicated through the network communication system 33. In another example, the drug monitoring unit 63, instead of the compliance monitoring logic 41, is configured to transmit notifications to the reminder unit 52. For example, the control logic 72 may determine that a dosage is due or has been missed and, in response, transmit a notification to remind the patient to take the due or missed dosage. The notification may be transmitted directly from the drug monitoring unit 63 to the reminder unit 52 (e.g., via RF signals), or the drug monitoring unit 63 may transmit the notification to the local base station 32. The local base station 32 may then transmit the notification directly to the reminder unit 52, or the base station 32 may transmit the notification to the reminder unit 52 through the network communication system 33.

Note that it is unnecessary for the drug monitoring unit 63 to store regime data 77. For example, in one embodiment, the control logic 72 monitors the sensors 86, 88 to determine when the patient takes dosages of the drug held by the container 56. In response to each detected dosage, the control logic 72 is configured to transmit data indicative of the dosage (e.g., the time and amount) to the compliance monitoring logic 41. The compliance monitoring logic 41, by comparing the data from the drug monitoring unit 63 to the regime data 152, determines when dosages are due and/or when dosages are missed.

It should be noted that the drug regime can be changed in real-time or "on the fly." For example, in one embodiment, the remote server 36 is at a physician's office. If the physician, for any reason, wishes to change the drug regime (e.g., change the amount and/or frequency of dosages), then the physician may provide an input for updating the regime. The compliance monitoring logic 41 appropriately updates the regime data 152 based on the input such that the future dosage times and amounts are consistent with the updated regime. The compliance monitoring logic 41 also transmits data indicative of the update through the network communication system 33 and the local base station 32 to the drug monitoring unit 63. In response, the control logic 72 updates the regime data 77 appropriately such that the future dosage times and amounts are consistent with the updated regime.

In addition, the regime data 77 and/or 152 may indicate how the drug regime is to be changed if the patient misses one or more dosages. For example, if a patient misses a dosage, it may be desirable to increase the frequency or drug amounts of the next few dosages. In one embodiment, the control logic 72 is configured to automatically implement the change in response to one or more missed dosages.

As a mere example, assume that the patient is to take one pill three times a day. Also assume that the regime data 77 indicates that one pill is due at 8:00 a.m., another pill is due at noon, and another pill is due at 5:00 p.m. Thus, at 8:00 a.m., noon, and 5:00 p.m., the control logic 72 daily sends a reminder notification indicating that a dosage of one pill is due if the user has not taken the dosage by the due time. Also assume that if the patient misses a dosage, then it is desirable that the user takes a pill four times the following day at the times of 8:00 a.m., 11:00 a.m., 2:00 p.m., and 5:00 p.m. Thus, instead of sending reminder notifications at 8:00 a.m., noon, and 5:00 p.m., the control logic 72 sends reminder notifications at 8:00 a.m., 11:00 a.m., 2:00 p.m., and 5:00 p.m. the day after the missed dosage.

In another example, instead of changing the dosages to four times a day, assume that it is desirable for the user to take two pills instead of one at 8:00 a.m. the day after missing a dosage. In such an example, the control logic 72 sends reminder notifications at the same times of 8:00 a.m., noon, and 5:00 p.m. the day after a missed dosage, but at the 8:00 a.m. dosage, the reminder notification indicates that the patient is to take two pills rather than one. Various other types of changes in the regime may be implemented in response to one or more missed dosages.

In one exemplary embodiment, the control logic 72, based on the drug sensor 86, determines when the amount of the drug being held by the container 56 falls below a specified threshold. In response to such a determination, the control logic 72 automatically transmits a notification message. For example, the control logic 72 may transmit the notification message to the remote server 36, which is located at a premise of a pharmacist, and the message may indicate to the pharmacist that the patient is about to run out of the drug in the container 56. Thus, the pharmacist may be provided with advanced notice that that the patient is about to come in for refill. The pharmacist may receive such messages from many patients thereby enabling to pharmacist to proactively address inventory issues. In addition, in response to such a notification message, the pharmacist may send a refill to the patient without the patient having to request such a refill from the pharmacist. In another example, the control logic 72 transmits the notification message to the reminder unit 52 to remind the patient to seek a refill from a pharmacist before the drug in the container 56 runs out. Rather than transmitting a message to the reminder unit 52, the control logic 72 may notify the patient that the amount of drug in the container 56 has fallen below a threshold amount via the output interface 94. For example, the control logic 72 may display a message to the patient. In another example, the control logic 72 activates a particular light source, such as an LED, which is used to signal a low amount of drug in the container 56. Various other techniques for providing a notification of a low amount of drug in the container 56 are possible in other examples.

In one exemplary embodiment, the control logic 72 is configured to sense when the patient is likely taking the wrong dosage relative to the regime indicated by the regime data 77. For example, the data 77 may indicate the amount of drug that is to be taken at each dosage. For each dosage, the control logic 72, based on the drug sensor 86, determines how much drug has been removed from the container 56. If the sensed amount is significantly greater or less than the expected amount, then the control logic 72 provides a warning indication.

In this regard, to determine whether to provide a warning indication, the control logic 72 is configured to determine, based on the sensor 86, the amount of drug removed from the container 56 for a particular dosage. The regime data 77 indicates an upper threshold that is greater than the amount of drug that should be taken for the dosage and a lower threshold that is less than the amount of drug that should be taken for the dosage. If the measured amount of dosage exceeds the upper threshold or is less than the lower threshold, then the control logic 72 is configured to provide a warning indication.

The warning indication can be in a variety of forms. For example, the control logic 72 may be configured to display a text message via the output interface 94. In another example, the output interface 94 comprises one or more light sources that are activated if the control logic 72 detects a wrong dosage. In one exemplary embodiment, the output interface 94 comprises a speaker, and the control logic 72 is configured to provide an audible warning, such as a buzzer or a prerecorded message, via the speaker. In another embodiment, the control logic 72 transmits a message to the reminder unit 52, which provides either an audible or visual indication. If the warning is noticed or received by the patient before consuming the drug, then it is possible that the patient will be deterred from consuming the wrong dosage. If the warning is noticed or received by the patient after consuming the drug, then at least the patient is warned that a wrong dosage has occurred, and the patient may take action in some way, such as calling a doctor to seek further instructions.

The control logic 72 is also configured to notify the compliance monitoring logic 41 at the remote server 36 of the wrong dosage. A user, such as a nurse or doctor, at the remote server 36 can evaluate whether any action should be taken in response to the wrong dosage. For example, the message transmitted to and displayed by the compliance monitoring logic 41 can indicate the amount and type of drug that the control logic 72 determined to have been removed from the container 56 for the wrong dosage. Based on such information, the user viewing the message may decide to take further action, such as calling the patient to verify the wrong dosage or check on the patient or to notify someone, such as emergency personnel or a friend, to check on the patient. Various other types of actions may be taken in response to a wrong dosage detection by the control logic 72.

In addition, a wrong dosage could occur as a result of the patient taking more dosages than those expected for the drug regime defined by the data 77. For example, if the data 77 indicates that a dosage is to be taken three times a day, then the control logic 72 may detect an occurrence of a wrong dosage if the patient takes four dosages. In this regard, assume that the patient has taken three dosages on a particular day and then removes the cap 61 to detect a fourth dosage, which is one more than what is expected for the desired regime. Upon detecting opening of the cap 61 via sensor 88, the control logic 72 may determine that a wrong dosage has occurred or is about to occur. In response, the control logic 72 may provide a warning indication, as indicated above. Accordingly, the patient may be warned prior to actually consuming the wrong dosage or can at least be notified that the wrong dosage has occurred.

As described above, it is possible for the logic 72 of the drug monitoring unit 63 to sense dosage occurrences and to report the dosages occurrences to the compliance monitoring logic 41. Any of the actions taken based on such dosage occurrences can be performed by either the control logic 72 of the drug monitoring unit 63 or the compliance monitoring logic 41, which is external to the drug monitoring unit 63. For example, it is possible for the compliance monitoring logic 41 to determine when a wrong dosage or some other event occurs to initiate a notification via the reminder unit 52 or the output device 94 of the drug monitoring unit 63.

An exemplary use of the system 20 will now be described with particular reference to FIG. 14.

For illustrative purposes, assume that a doctor prescribes to a patient a drug, in the form of liquid, that is to be taken three times a day (morning, midday, and evening) at 20 milliliters (ml) per dosage. The patient takes the prescription to a pharmacist who fills the prescription. In filling the prescription, the pharmacist pours the drug into the container 56 and attaches the container 56 to the drug monitoring unit 63. The pharmacist also downloads the regime data 77 into the drug monitoring unit 63. The regime data 77 indicates that 20 ml is to be taken three times per day for a particular number of days. In the instant example, assume that the data indicates several time periods per dosage.

In this regard, assume that the data 77 indicates three reminding times: 8:00 a.m., noon, and 5:00 p.m. In addition, the data 77 defines dosage intervals that respectively begin one hour before each scheduled dosage time and end one hour after each such scheduled dosage time. For example, for the morning dosage, the dosage interval begins at 7:00 a.m. and ends at 9:00 a.m. The dosage interval represents the acceptable interval within which the patient may take the dosage correlated with the interval. For example, for the morning dosage, the patient may take the dosage between 7:00 a.m. and 9:00 a.m. In other words, the morning dosage is due between 7:00 a.m. and 9:00 a.m. If 9:00 a.m. is reached without a dosage being taken between 7:00 a.m. and 9:00 a.m., then the morning dosage is deemed to have been missed.

Figure 14:
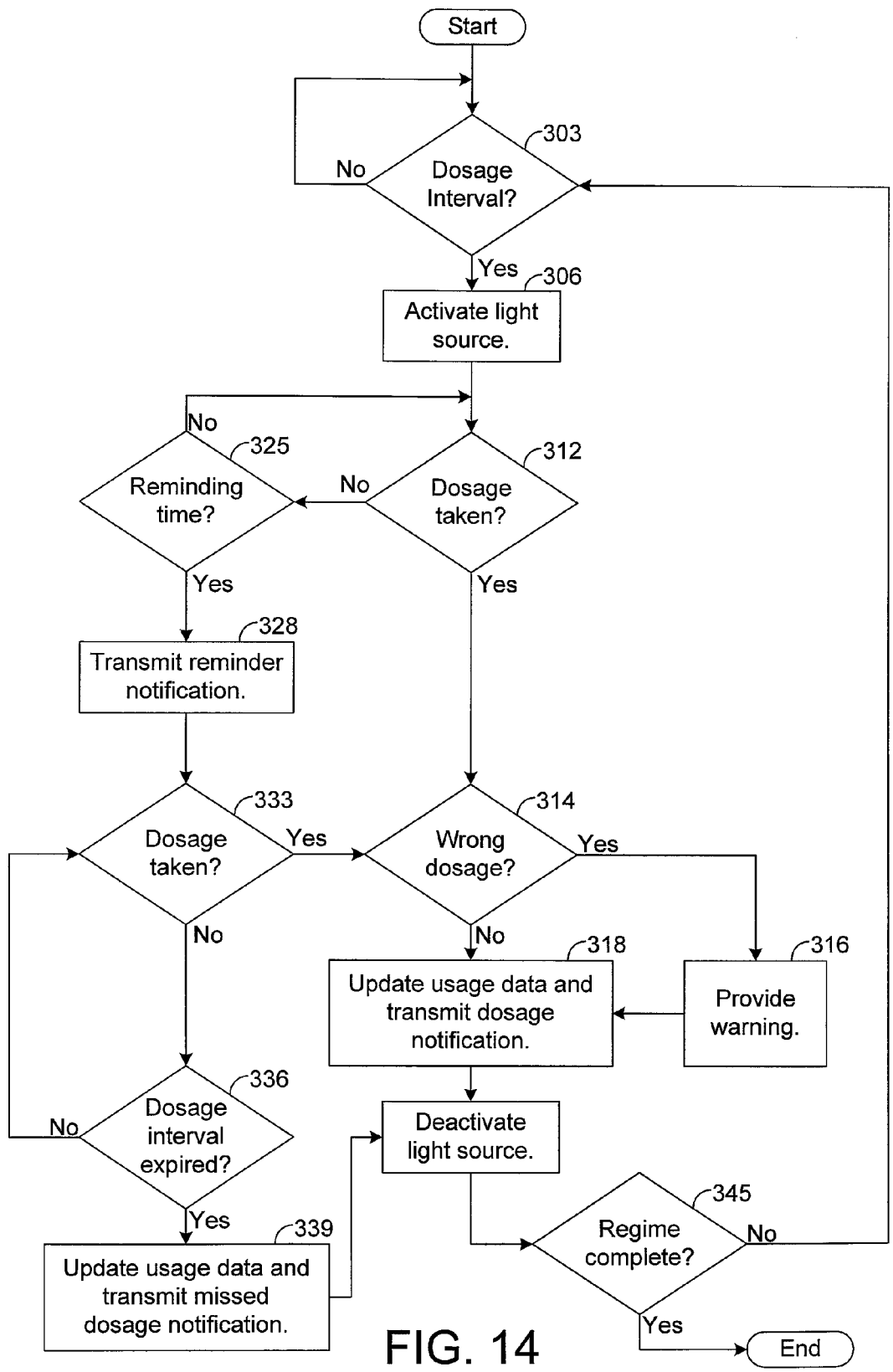
FIG. 14 is a flow chart illustrating an exemplary method for monitoring compliance to an expected drug regime.

Initially, the control logic 72 monitors time, based on the clock 83, to determine when a dosage interval begins, as shown by block 303 of FIG. 14. In the instant example, the control logic 72 makes a "yes" determination in block 303 at 7:00 a.m. In response, the control logic 72 provides an indication, via the output interface 94, that the container 56 is holding a drug for which the user may take a dosage in order to comply with the predefined drug regime for the drug. In other words, the control logic 72 provides an indication that a dosage is due. For the instant example, assume that such an indication is provided by activating the light source 95, as shown by block 306 of FIG. 14. In other embodiments, the dosage due indication may be in the form of a text message displayed by output interface 94 or some other type of indication.

In block 312, the control logic 72 determines whether the patient has taken a dosage from the container 56 since the beginning of the current dosage interval. Such a determination may be based on the drug sensor 86 and/or the container sensor 88. For example, in one embodiment, the control logic 72 makes a "yes" determination in block 312 when the drug sensor 86 senses a reduction of the drug in the container 56 while the container sensor 88 senses that the cap 61 is removed from the container 56. In another embodiment, the control logic 72 may make a "yes" determination in block 312 when the drug sensor 86 senses a reduction of the drug in the container 56 or when the container sensor 88 senses that the cap 61 is removed from the container 56.

If the patient takes a dosage between 7:00 a.m. and 8:00 a.m., the control logic 72 makes a "yes" determination in block 312 in response to such dosage. Thus, the control logic 72 checks to determine whether the correct dosage amount has been taken, as shown by block 314. If not, the control logic 72 provides a warning, as shown by block 316, via output interface 94 or otherwise. For example, the control logic 72 may immediately activate a buzzer or some other type of sound producing device. The control logic 72, in addition to or in lieu of an audio warning, may provide a visual warning such as activating one or more light sources or displaying a text message. In addition to or in lieu of providing a warning via output interface 94, the control logic 72 may also transmit a warning indication to the reminder unit 52, which provides a visual and/or audio warning to the patient. The control logic 72 may also transmit a warning indication to the compliance monitoring logic 41, which then takes some action such as triggering an alarm to bring attention to the detected occurrence. Such an alarm could be a visual and/or audio indication. Other actions in response to a wrong dosage detection are possible.

After detecting a dosage in block 312, the control logic 72 updates the usage data 91 to indicate that the patient has taken a dosage and transmits a notification, referred to hereafter as a "dosage notification," to the compliance monitoring logic 41, as shown by block 318 of FIG. 14. As shown by block 322 of FIG. 14, after the detected dosage, the control logic 72 of the drug monitoring unit 63 deactivates the light source 95 to indicate that a dosage from the container 56 is no longer currently due.

In updating the usage data 91, the control logic 72 indicates the time of the sensed dosage and the amount of drug removed from the container 56, as sensed by the drug sensor 86. This same information is also included in the dosage notification, which is transmitted by the wireless communication interface 75 to the local base station 32. The local base station 32 reformats the dosage notification, if necessary, for transmission through the network communication system 33. In one example, the dosage notification is to be transmitted via the Internet, and the local base station 32 packetizes the dosage notification into one or more data packets in accordance with Internet Protocol (IP). Other notifications may be similarly processed by the base station 32. Upon receiving the dosage notification, the compliance monitoring logic 41 updates the usage data 155 stored at the remote server 36.

As shown by blocks 312, 325, as the control logic 72 is checking for a dosage based on the sensors 86, 88, the control logic 72 determines in block 325 whether the reminding time has been reached. In the instant example, the reminding time is 8:00 a.m. Thus, if a dosage is not sensed via sensors 86, 86 between 7:00 a.m. and 8:00 a.m., the control logic 72 makes a "yes" determination in block 325 at 8:00 a.m. In response, the control logic 72 transmits a notification, referred to hereafter as a "reminder notification," to the reminder unit 52, as shown by block 328. The reminder notification indicates that a dosage from the container 56 is currently due. In one embodiment, the reminder notice includes the expected time of the dosage (i.e., 7:00 a.m. to 9:00 a.m. in the instant example), the type of drug for the dosage, and the amount of drug that is to be consumed for the dosage. As an example, the control logic 72 may transmit a text message including such information to the reminder unit 52. In other embodiments, other types of information may be communicated, and other types of notifications may be employed.

Accordingly, if the patient has not taken a dosage during the dosage interval and prior to the reminding time, the patient is provided with a reminder that a dosage is currently due. In addition, the control logic 72 may be configured to transmit additional reminder notifications to the reminder unit 52 if desired.

After a reminder notification has been transmitted in block 328, the control logic 72 continues checking for a dosage based on sensors 86, 88, as shown by block 333. As shown by block 336, the control logic 72 also checks whether the dosage interval has expired. In the instant example, the dosage interval expires at 9:00 a.m. If a dosage is sensed before expiration of the dosage interval, then the control logic 72 checks for whether the correct dosage has been taken, updates the usage data 91, and transmits a dosage notification to the compliance monitoring logic 41, as described above and shown by blocks 314, 318. The control logic 72 also deactivates the light source 95 in block 322.

If the dosage interval expires without the control logic 72 having detected a dosage based on the sensors 86, 88, then the control logic 72 updates the usage data 91 and transmits at least one missed dosage notification, as shown by block 339. In this regard, the control logic 72 transmits a text message indicating the time of the current dosage and the fact that the dosage has now been missed. The text message is transmitted to the reminder unit 52, which displays the text message to the patient. Other types of messages and/or indications may be transmitted to the reminder unit 52 in other examples. In addition, the missed dosage notification is transmitted from the wireless communication interface 75 to the local base station 32, which transmits the notification through the network communication system 33 to the reminder unit 52. In other embodiments, other communication techniques may be employed, such as transmitting the notification directly to the reminder unit 52 from the local base station 32 or the wireless communication interface 75.

In updating the usage data 91 in block 339, the control logic 72 indicates in the data 91 that the dosage was missed. In this regard, the usage data 91 may have an entry for each dosage that is to be taken as part of the expected drug regime. For each dosage, the control logic 72 stores, in the dosage's entry, the time that the dosage was taken and the amount of the drug removed from the container 56 for the dosage. If the dosage is missed, the control logic 72 may store a value of zero for the amount of drug taken or otherwise indicate that the dosage was missed.

In addition or in lieu of transmitting a missed dosage notification to the reminder unit 52, the control logic 72 also transmits a missed dosage notification to the compliance monitoring logic 41. The logic 41 updates the usage data 155 stored at the remote server 36. For example, the compliance monitoring logic 41 may update the data 155 in the same or similar way that the control logic 72 updates the data 91 for each dosage. The compliance monitoring logic 41 may take additional actions in response to the missed dosage, if desired. For example, the logic 41 may attempt to contact the patient and/or a caregiver of the patient to inform them of the missed dosage.

Note that after determining that the current dosage has been missed, the control logic 72 may be configured to take some action, such as providing the patient with instructions on how to compensate for the missed dosage. Such instructions may be transmitted to the reminder unit 52, displayed via the output interface 94, or otherwise conveyed to the patient. For example, the instructions may indicate that the patient is to take a higher amount of drug for the next dosage. The control logic 72, in response to the missed dosage determination, may also change the times and/or amounts of one or more future dosages indicated by the data 77. Information indicating how the control logic 72 is to handle a missed dosage may be included in the data 77. In other embodiments, the compliance monitoring logic 41 may be configured to take similar actions, such as updating the drug regime, based on the missed dosage notification.

After detecting a dosage during the dosage interval or expiration of the dosage interval, the control logic 72 deactivates the light source 95, as shown by block 322. Thereafter, the logic 72 repeats the aforementioned process for each subsequent dosage until the regime has been completed, as shown by block 345.

Moreover, the various embodiments described above allow a patient's compliance to an expected drug regime to be monitored. Such monitoring can be used to assist the patient in complying with the expected regime as well as to provide warnings or notifications when the patient fails to comply with the expected regime. It should be apparent to one or ordinary skill in the art that various changes could be made to the exemplary embodiments described above.

Now, therefore, the following is claimed:

1. A drug containment unit, comprising:
a drug container;
memory coupled to the drug container, the memory for storing data indicative of when dosages of a drug held by the container are to be removed from the container in accordance with an expected drug regime;
a sensor coupled to the drug container, the sensor configured to sense a parameter indicating when a portion of the drug is removed from the container; and
logic coupled to the drug container, the logic configured to monitor the parameter sensed by the sensor and to automatically trigger, based on the data and the parameter sensed by the sensor, a reminder notification for reminding a user to take at least one dosage of the drug, the logic configured to determine a value indicative of an amount of the drug removed from the drug container and to perform a comparison between the value and the data to determine whether the amount of the drug removed from the drug container is consistent with the expected drug regime, the logic further configured to trigger, based on the comparison, a real-time notification for warning the user prior to consuming the amount of the drug removed from the drug container if the comparison indicates that the amount of the drug removed from the drug container is inconsistent with the expected drug regime.

2. The drug containment unit of claim 1, wherein the sensor is configured to automatically sense an amount of the drug held by the container.

3. The drug containment unit of claim 1, wherein the sensor comprises a plurality of electrodes, wherein the sensor is configured to sense a capacitance between the electrodes, and wherein the logic is configured to estimate an amount of the portion of the drug removed from the container based on the capacitance between the electrodes.

4. The drug containment unit of claim 1, wherein the logic is mounted on a frame that is detachably coupled to the drug container.

5. The drug containment unit of claim 1, further comprising an output device coupled to the drug container, wherein the reminder notification is communicated to the user via the output device.

6. The drug containment unit of claim 1, further comprising a light source coupled to the drug container, wherein the logic is configured to activate the light source in response to a determination by the logic that a dosage of the drug is currently due.

7. The drug containment unit of claim 1, wherein the reminder notification is wirelessly transmitted to a portable reminder unit when the portable reminder unit is carried by a user and not coupled to the drug container, the memory, the sensor, and the logic.

8. The drug containment unit of claim 1, wherein the logic is configured to determine the value based on the sensor.

9. The drug containment unit of claim 8, wherein the data comprises a threshold, and wherein the logic is configured to compare the value and the threshold to determine whether the amount is consistent with the expected drug regime.

10. The system of claim 7, wherein the portable reminder unit comprises a cellular telephone.

11. The system of claim 7, wherein the portable reminder unit comprises a pager.

12. The system of claim 1, wherein the logic is configured to determine whether a dosage of the expected drug regime is missed, and wherein the logic is configured to automatically change the expected drug regime in response to a determination that the dosage of the expected drug regime has been missed.

13. A drug containment unit, comprising:
a drug container;
a plurality of electrode coupled to the drug container; and
logic configured to determine when a first portion of a drug has been removed from the container, the logic further configured to estimate an amount of the first portion based on a measurement of a capacitance between the electrodes and to transmit a notification based on a determination that the portion of the drug has been removed from the container.

14. The drug containment unit of claim 13, further comprising a communication interface coupled to the drug container, the communication interface configured to wirelessly transmit the notification to a portable reminder unit that is not coupled to the drug container.

15. The system of claim 13, wherein the logic is configured to provide the notification in real-time in response to a determination that the first portion removed from the container is inconsistent with an expected drug regime such that a user who removes the first portion from the drug container receives the notification prior to consuming the first portion.

16. The drug containment unit of claim 13, wherein the measurement of the capacitance is performed while a second portion of the drug remains in the cavity between the electrodes, and wherein the second portion of the drug affects the measurement of the capacitance.

17. A drug compliance monitoring system, comprising:
a drug container;
a sensor coupled to the drug container, the sensor configured to sense a parameter indicative of when a user takes dosages of a drug in the container;
a portable reminder unit attached to a user and not coupled to the drug container and the sensor;
memory for storing data indicative of an expected drug regime; and
logic configured to perform at least one comparison between the data and the parameter sensed by the sensor, the logic further configured to transmit, to the reminder unit based on the at least one comparison, a reminder notification for reminding the user to take a dosage of the drug.

18. The system of claim 17, further comprising a light source coupled to the drug container, wherein the logic is configured to activate the light source in response to a determination by the logic that a dosage of the drug is currently due.

19. The system of claim 17, wherein the drug container has a cavity for receiving the drug, wherein the drug container has a removable cap covering a mouth of the cavity, wherein the sensor comprises a plurality of electrodes positioned such that the drug is between the electrodes when the drug is inserted into the cavity, wherein the sensor is configured to sense a capacitance between the electrodes while at least a portion of the drug remains in the cavity, and wherein the value is based on the sensed capacitance.

20. The system of claim 17, wherein the logic is mounted on a frame that is detachably coupled to the drug container.

21. The system of claim 17, wherein the logic is configured to determine when the user deviates from the expected drug regime based on the at least one comparison.

22. The system of claim 21, wherein the logic is configured to automatically update the expected drug regime in response to a determination that the user has deviated from the expected drug regime.

23. The system of claim 17, wherein the logic is configured to determine, based on the parameter sensed by the sensor, a value indicative of an amount of the drug removed from the drug container.

24. The system of claim 23, wherein the logic is configured to perform a comparison between the value and a threshold and to transmit, based on the comparison, a notification for warning the user that an unexpected amount of the drug has been removed from the drug container.

25. The system of claim 17, wherein the logic is configured to determine a value indicative of an amount of the drug removed from the drug container and to perform a comparison between the value and the data to determine whether the amount of the drug removed from the drug container is consistent with the expected drug regime, the logic further configured to trigger, based on the comparison between the value and the data, a real-time notification for warning the user prior to consuming the amount of the drug removed from the drug container if the comparison between the value and the data indicates that the amount of the drug removed from the container is inconsistent with the expected drug regime.

26. A method, comprising the steps of:
storing data indicative of expected dosage times for a drug held by a drug container;
automatically sensing actual dosage times for the drug;
comparing, based on the sensing step, the actual dosage times to the expected dosage times indicated by the data;
transmitting at least one notification based on the comparing step;
sensing an amount of the drug removed from the drug container by a user;
comparing the sensed amount to an expected dosage amount for the expected drug regime;

determining whether the sensed amount is consistent with the expected dosage amount; and providing a real-time notification for warning the user prior to consuming the amount of the drug removed from the drug container if the sensed amount is determined to be inconsistent with the expected dosage amount.

27. The method of claim 26, further comprising the steps of:

receiving the transmitted notification at a portable reminder unit while the portable reminder unit is being carried by the user; and outputting, from the portable reminder unit and based on the transmitted notification, information for reminding a user to take a dosage of the drug.

28. The method of claim 26, further comprising the step of activating a light source coupled to the drug container based on the comparing the actual dosage times to the expected dosage times step.

29. The method of claim 26, wherein the sensing the amount of the drug step is based on a capacitance between a plurality of electrodes coupled to the drug container.

30. The method of claim 26, further comprising the steps of:

determining that at least one of the expected dosage times is missed; and automatically changing the expected drug regime in response to the determining that the at least one of the expected dosage times is missed step.

31. The method of claim 29, wherein the sensing the amount of the drug step comprises the steps of:

sensing the capacitance between the electrodes while at least a portion of the drug remains in the drug container between the electrodes after the amount of the drug has been removed from the drug container; and estimating the amount of the drug removed from the drug container based on the sensed capacitance, wherein the sensed capacitance is affected by the portion of the drug that remains in the drug container between the electrodes after the amount of the drug has been removed from the drug container.

* * * * *